United States Patent [19]

Bohn

[11] Patent Number: 4,524,027
[45] Date of Patent: Jun. 18, 1985

[54] MEMBRANE-ASSOCIATED PROTEINS (MP₂), A PROCESS FOR OBTAINING THEM, AND THEIR USE

[75] Inventor: Hans Bohn, Marburg, Fed. Rep. of Germany

[73] Assignee: Behringwerke Aktiengesellschaft, Marburg, Fed. Rep. of Germany

[21] Appl. No.: 653,037

[22] Filed: Sep. 21, 1984

[30] Foreign Application Priority Data

Sep. 23, 1983 [DE] Fed. Rep. of Germany ....... 3334405

[51] Int. Cl.³ .................. C07G 7/00; A61K 35/42; A61K 35/50; A61K 39/395
[52] U.S. Cl. ......................... 260/112 R; 260/112 B; 424/85; 424/88; 424/105; 424/101; 436/543; 436/547
[58] Field of Search .............. 260/112 R, 112 B; 424/85, 88, 101, 105

[56] References Cited

U.S. PATENT DOCUMENTS

| | | | |
|---|---|---|---|
| 4,041,021 | 8/1977 | Bohn | 260/112 B |
| 4,065,445 | 12/1977 | Bohn et al. | 260/112 B |
| 4,191,533 | 3/1980 | Bohn et al. | 260/112 B X |
| 4,254,021 | 3/1981 | Bohn et al. | 260/112 B |
| 4,269,825 | 5/1981 | Bohn et al. | 424/85 |
| 4,297,274 | 10/1981 | Bohn et al. | 260/112 B |
| 4,297,343 | 10/1981 | Bohn et al. | 424/85 |
| 4,301,064 | 11/1981 | Bohn | 260/112 R |
| 4,302,385 | 11/1981 | Bohn et al. | 260/112 B |
| 4,309,339 | 1/1982 | Haupt et al. | 260/112 B |
| 4,325,866 | 4/1982 | Bohn | 260/112 B |
| 4,348,316 | 9/1982 | Bohn | 260/112 R |
| 4,368,148 | 1/1983 | Bohn | 260/112 B |
| 4,468,345 | 8/1984 | Bohn et al. | 260/112 R |
| 4,481,137 | 11/1984 | Ohnishi et al. | 260/112 R |

OTHER PUBLICATIONS

Bohn, Protides Biol. Fluids, 24, 117–124, (1976).
Bohn, Arch. Gynaekol. 212, 165–175, (1972), 221, 73–81, (1976), 218, 131–142, (1975).
Bohn, Blut. 24, 292–302, (1972).

*Primary Examiner*—Howard E. Schain
*Attorney, Agent, or Firm*—Finnegan, Henderson, Farabow, Garrett & Dunner

[57] ABSTRACT

Membrane-associated proteins, called MP₂, and a process for obtaining them are described. The proteins have the following parameters:

(a) an electrophoretic mobility in the range between that of $\alpha_2$ and that of $\beta_1$ globulins;
(b) an isoelectric point in the pH range 4.4–5.0;
(c) a sedimentation coefficient $s_{20,w}$ in the range from 7 to above 20 S, the main fractions (IV, III, II and I) sedimenting at about 7, 9, 14 and 20 S respectively;
(d) molecular weights in the range from 200,000 to 1,000,000, the main fractions (IV, III, II and I) having molecular weights of about 210,000, 400,000, 750,000 and 1,000,000;
(e) an extinction coefficient $E_{1\,cm}^{1\%}$ (280 nm) of 12.5±0.2;
(f) a carbohydrate content of 8.0±3.2% (mannose 1.4±0.4%, fucose 0.4±0.2%, galactose 1.2±0.4%, N-acetylglucosamine 2.6±1.8%, and N-acetylneuraminic acid 2.4±1.4%) and
(g) aminoacid composition in which aspartic acid, glutamic acid, leucine, valine, serine and glycine are among the aminoacids present in greatest amounts.

These proteins can be used to prepare antisera which can be used to detect and determine these proteins or their components. Furthermore, antibodies reacting with these proteins can be used for diagnosis, monitoring the progress of a disease or checking therapy.

3 Claims, 1 Drawing Figure

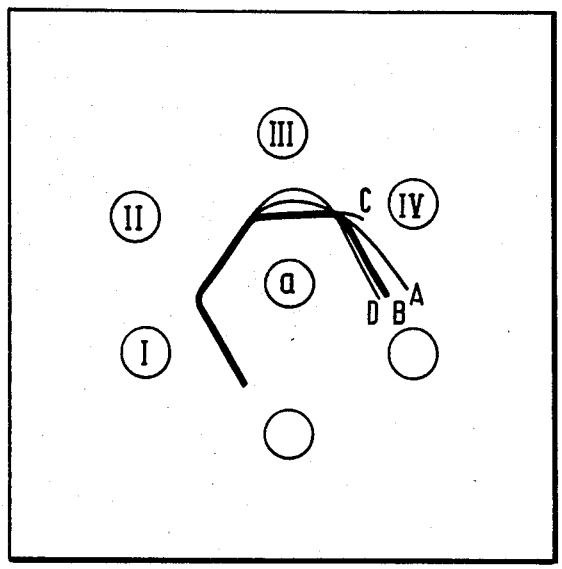
I–IV MP$_2$-Fractions
a = Rabbit Anti-MP$_2$-serum

MEMBRANE-ASSOCIATED PROTEINS (MP₂), A PROCESS FOR OBTAINING THEM, AND THEIR USE

The invention relates to a group of membrane-associated tissue proteins from the human placenta. It also relates to a process for obtaining these proteins. The proteins can be used to obtain antisera and antibodies which can be used for the detection and determination of the proteins.

Two membrane-associated proteins, called MP₁ and PP₄, are disclosed in German patent application Nos. 3,314,293 and 3,315,000.

The proteins described in this text differ from the latter in their physical, chemical and immunochemical properties. Moreover, they are not identical to other known structural proteins of human tissue, such as collagen, fibrin, fibronectin, actin or laminin, from which they likewise differ in their physical, chemical or immunochemical properties.

The group of membrane-associated tissue proteins (MP₂) from the human placenta, which have a complex composition and are described in the present patent application, show considerable differences in respect of their sedimentation coefficients and molecular weights, but they are immunochemically identical or partially related and, moreover, they greatly resemble one another in their other physical properties and their chemical composition.

The MP₂ proteins can be separated by gel filtration into four fractions (I to IV) which are clearly separated from one another. The structure of these proteins involves a total of at least four different components which differ in their antigenic determinants.

The invention relates to a group of proteins, called MP₂, which have the following characteristics:

(a) an electrophoretic mobility in the range between that of $\alpha_2$ and that of $\beta_1$ globulins;

(b) an isoelectric point in the pH range 4.4–5.0;

(c) a sedimentation coefficient $s_{20,w}^c$ in the range from 7 to above 20 S, the main fractions (IV, III, II and I) sedimenting at about 7, 9, 14 and 20 S respectively;

(d) molecular weights in the range from 200,000 to 1,000,000, the main fractions (IV, III, II and I) having molecular weights of about 210,000, 400,000, 750,000 and 1,000,000;

(e) an extinction coefficient $E_{1cm}^{1\%}$ (280 nm) of 12.5±0.2;

(f) a carbohydrate content of 8.0±3.2% (mannose 1.4±0.4%, fucose 0.4±0.2%, galactose 1.2±0.4%, N-acetylglucosamine 2.6±1.8%, and N-acetylneuraminic acid 2.4±1.4%) and (g) an aminoacid composition in which aspartic acid, glutamic acid, leucine, valine, serine and glycine are among the aminoacids present in greatest amounts.

By way of example, Table I shows the results of the aminoacid analyses for fractions II and IV.

TABLE 1

| Aminoacid | Residues per 100 residues (mole %) | |
|---|---|---|
| | Fraction II | Fraction IV |
| Cysteine | 2.80 | 3.55 |
| Methionine | 1.80 | 1.55 |
| Tryptophan | 2.60 | 2.95 |
| Aspartic acid | 10.75 | 10.15 |
| Threonine | 4.85 | 4.55 |
| Serine | 7.50 | 8.15 |
| Glutamic acid | 9.20 | 9.70 |
| Proline | 5.45 | 6.25 |
| Glycine | 6.70 | 7.70 |
| Alanine | 6.40 | 6.05 |
| Valine | 7.35 | 7.30 |
| Isoleucine | 4.90 | 4.65 |
| Leucine | 8.95 | 7.90 |
| Tyrosine | 3.35 | 3.25 |
| Phenylalanine | 4.45 | 3.80 |
| Histidine | 2.45 | 2.65 |
| Lysine | 5.50 | 5.60 |
| Arginine | 4.90 | 4.25 |

The following may be detailed to illustrate the characterizing features of the MP₂ tissue proteins:

The electrophoretic mobility was determined on cellulose acetate films (supplied by Sartorius) using sodium diethylbarbiturate buffer, pH 8.6, with a Microzone R 200 apparatus from Beckman Instruments.

The isoelectric point was determined using a column (440 ml) supplied by LKB, Stockholm. The Ampholin® mixture had a pH range from 4.0 to 6.0.

The sedimentation coefficient was determined in an analytical ultracentrifuge supplied by Beckman (Spinco apparatus, model E) at 60,000 rpm in double-sector cells using the UV scanner technique at 280 nm. The solvent used was water. The protein concentration was 2 g/l.

The behavior on gel filtration and in the ultra-centrifuge and the electrophoretic migration in SDS-containing polyacrylamide gel were used to determine or estimate the molecular weights. The gels used in the latter method contained 7.5 or 10 g/100 ml polyacrylamide (PAA) and 0.1 g/100 ml sodium dodecyl sulfate (SDS). To determine the molecular weights of the native proteins the MP₂ fractions I–IV were applied dissolved in water or 0.01 mol/l tris buffer. The comparison substances used were ferritin (MW 450,000), the subunit S (MW 180,000) of the fibrin-stabilizing factor, the pregnancy-specific $\beta_1$-glycoprotein (MW 90,000) and human albumin.

To determine the extinction coefficient, 1 mg of substance was dissolved in distilled water to produce 1 ml of solution.

The carbohydrates were determined as follows: After hydrolysis of the glycosidic bonds, the liberated neutral sugars were separated as the borate complexes in an anion exchanger column (Y. C. Lee et al., Anal. Biochem. 27 (1969), 567), converted into a colored complex in the eluate by admixture of Cu(I) bicinchoninate reagent (K. Mopper and M. Gindler, Anal. Biochem. 56 (1973), 440) and determined quantitatively using rhamnose as the internal standard. The aminosugars were detected and determined by their reaction with ninhydrin. The neuraminic acid content was determined by the method of Warren (Methods in Enzymology, Vol. VI (1963), 463–465).

The aminoacid analyses were carried out by the method of S. Moore, D. H. Spackman, W. H. Stein, Anal. Chem. 30 (1958), 1185, using a Multichrom B liquid chromatograph supplied by Beckman. Cystine was determined as cysteic acid after oxidation of the proteins with performic acid (S. Moore et al., Anal. Chem. 30 (1958), 1185) followed by chromatography (S. Moore, J. Bio. Chem. 238 (1963), 235). The tryptophan content was determined by direct photometry using the method of H. Edelhoch, Biochemistry 6 (1967), 1948.

The invention also relates to a process for obtaining the membrane-associated placental proteins $MP_2$, which comprises 1. comminuting fully developed human placentae as are produced at delivery, washing with physiological saline until all the soluble constituents have been removed, and extracting the tissue residue thus obtained with a solution containing 0.5–5 g of a non-ionic detergent per 100 ml, preferably with a solution containing 2 ml/100 ml polyethylene glycol p-isooctylphenyl ether, removing the supernatent, dialyzing it against water or buffer solution, and concentrating it;
2. further concentrating, by immunoadsorption, the solubilized placental tissue antigens contained in the resulting solution;
3. subjecting the solution, which is concentrated in antigens after the immunoadsorption, to gel filtration and, at the same time, essentially removing other solubilized proteins of the placenta ($MP_1$, $PP_4$) which have a smaller molecular weight; and
4. where appropriate, removing the accompanying proteins (traces of immunoglobulins and of membrane-associated protein $MP_1$ and, in particular, ferritin, which appears in the $MP_2$ fraction III) which are occasionally still present as impurities in the $MP_2$ fractions, by inverse immunoadsorption, i.e. by carrier-bound antibodies against these accompanying proteins, and thus obtaining the $MP_2$ fractions free of impurities.

Apart from the parameters indicated, it is also possible to use immunochemical methods to detect the $MP_2$ proteins, for example in a fraction from a separating operation, since the $MP_2$ proteins have antigenic properties.

A total of at least 4 components (A, B, C and D) are involved in the structure of the $MP_2$ proteins, these components differing in their antigenic determinants. Table 2 shows the distribution of these different antigenic regions in the $MP_2$ fractions I–IV. Fractions I–III contain all four antigenic regions. Component A appears to be present in the largest amount. In contrast, component B predominates in fraction IV. Component C is virtually completely absent from this fraction.

TABLE 2

| Distribution of the antigenic regions A, B, C and D in $MP_2$ fractions I–IV | | | |
|---|---|---|---|
| A | B | C | D |
| I | ++ | + | + | (+) |
| II | ++ | + | + | (+) |
| III | ++ | (+) | + | (+?) |
| IV | + | ++ | − | + |

++ present to a very large extent, + large extent, (+) small extent and − absent Accordingly, by immunization of rabbits with purified fractions I–IV, it is possible to obtain antisera which contain variable amounts of antibodies against the antigenic regions A, B, C and D or even against only some of these components. It is possible to make these antisera specific against one or other of the antigenic regions by suitable absorption with appropriate placental fractions or $MP_2$ fractions. Monoclonal antibodies which each react with only one of the antigenic determinants contained in these proteins are obtained by fusing spleen cells of mice, which have been immunized with $MP_2$ proteins, with mouse myeloma cells and then selecting and further multiplying the hybrid cells formed. A procedure of this type has been described by, for example, Köhler and Milstein in Nature, Vol. 256 (1975), 495–497.

The $MP_2$ proteins can then be used to prepare antisera against the totality or against individual fractions and components of these protein complexes or to obtain antibodies which each react with only one of the antigenic determinants contained in these proteins (monoclonal antibodies).

The antisera and antibodies can be used to localize the $MP_2$ proteins, or proteins which are antigenically related to them, in tissues, and to detect and determine them in body fluids. Furthermore, these antisera and antibodies can be used to prepare immunoadsorbents with the aid of which it is possible to isolate from tissue extracts or body fluids proteins which are immunochemically identical to $MP_2$ or are partially related to $MP_2$.

It is possible to use, for example, the Ouchterlony gel diffusion test for the immunochemical detection of the $MP_2$ proteins with precipitating antibodies. FIG. 1 shows the immunological reaction, in this test, of the $MP_2$ fractions I–IV with an antiserum obtained by immunization of rabbits with fraction II. In the case of the higher molecular weight fractions I and II, the precipitates with the various antigenic regions essentially coincide in one line, while the lines of precipitation with the lower molecular weight fractions III and IV are separate from one another to some extent. The assignment of the individual lines to the different antigenic regions A, B, C and D is shown in FIG. 1.

It is also possible to use more sensitive immunochemical methods, such as radioimmunoassays or enzyme immunoassays, to detect the $MP_2$ proteins or proteins which are partly immunologically related to them.

The detection and the determination of the $MP_2$ proteins or antigens which are partially related to them are of diagnostic importance. $MP_2$ proteins or proteins which are immunochemically identical or related to them occur in relatively large concentrations in certain human organs; for example in the embryonal gastrointestinal tract and in the kidney of adult humans. When these organs are diseased, elevated concentrations of the $MP_2$ antigens can appear in the serum or in the urine as a result of increased cell destruction. Thus the detection and determination of these antigens in body fluids can be used to detect diseases in organs of these types, to monitor the progress of the disease and to check the therapy. Proteins related to $MP_2$ occur in most other human organs either not at all or only in traces. Thus, the $MP_2$ proteins can be used to prepare antisera and antibodies which can be used to detect and determine $MP_2$ proteins or their components by immunochemical methods.

On the other hand, antibodies against $MP_2$ proteins and their components can be used to prepare immunoadsorbents which can be used to isolate immunologically identical or partially related proteins. The invention is illustrated by the Example which follows:

EXAMPLE 1.1 Comminution and washing of the placentae

Mature human placentae as are produced at delivery were used for the isolation of the membrane-associated proteins $MP_2$. The placentae were first frozen at −20°

C., then comminuted in the frozen state using a cutter-mixer and stored in this form at −20° C. until used. In the first place, all soluble tissue proteins were removed by washing with physiological NaCl solution. For this purpose, 700 ml of NaCl solution were added to 500 g of the comminuted placental tissue which was briefly homogenized and then stirred at 4° C. for several hours and finally centrifuged. The supernatent was discarded, and the residue was again stirred with 700 ml of NaCl solution for several hours and again centrifuged. This washing procedure was repeated a total of 6 times. The soluble constituents were essentially removed from the placental tissue in this manner.

1.2 Extraction of the placental tissue with Triton ® X-100

The tissue residue was extracted three times with 700 ml each time of a solution of 2 ml of polyethylene glycol p-isooctylphenyl ether (Triton X-100) in 100 ml of water, each time the mixture being stirred at 4° C. for 20 hours and then centrifuged. The extracts were first dialyzed against water and then against a 0.1 mol/l tris HCl buffer (pH 8.0) which contained 1 mol/l NaCl and 1 g/l sodium azide (buffer solution II). The dialyzates were each concentrated to about 200 ml using an ultrafilter (supplied by Amicon) with PM-10 membranes and were then combined (fraction A).

2. Concentration of the MP$_2$ proteins by immunoadsorption 2.1 Preparation of the immunoadsorbent Polyvalent antisera were prepared by immunization of rabbits with the solubilized placental protein fraction A. The antisera contained antibodies against both the MP$_2$ proteins and other tissue antigens which had been solubilized with Triton ® X-100. 350 ml of an antiserum pool of this type were dialyzed against 0.02 mol/l phosphate buffer (pH 7.0) and chromatographed on DEAE cellulose using the same buffer to remove the immunoglobulins. The immunoglobulin fraction which passed through (3.63 g protein) was then reacted with 363 g of specially purified agarose in the form of beads (Sepharose ® from Pharmacia, Uppsala, Sweden) which had been activated with 45.3 g of cyanogen bromide, and was thus covalently bonded to a carrier. The procedure has been described by Axen et al., Nature 214 (1967) 1302. The MP$_2$ proteins, together with other solubilized antigens from placental fraction A, could be further concentrated using an immunoadsorbent prepared in this manner.

2.2 Procedure for immunoadsorption

The immunoadsorbent was suspended in buffer solution II, filled into a chromatography column (5.0×20 cm) and washed with buffer solution II. Then one third of fraction A was applied to the column, whereupon the MP$_2$ proteins and other solubilized antigens were bound by immunoadsorption. The column was then thoroughly washed with buffer II. Then the adsorbed proteins were eluted from the column using about 600 ml of 6 mol/l urea solution. The eluates containing MP$_2$ were dialyzed against buffer solution II and concentrated to about 20 ml using an ultrafilter. The yield per adsorption was about 20-40 mg of protein.

The adsorbent in the column was again thoroughly washed with buffer solution II immediately after the elution of the proteins. It was then reused for the binding of solubilized antigens by immunoadsorption.

3. Gel filtration of the MP$_2$ proteins

The MP$_2$ proteins which had been concentrated by immunoadsorption were separated on the basis of their different molecular weights by gel filtration on acrylamide-agarose AcA-34 (LKB, Stockholm) into 4 fractions (I-IV) which were clearly separated from one another. In this, fraction I came off the column immediately after the void volume. Most of the other solubilized membrane antigens (MP$_1$ and PP$_4$) had molecular weights below 200,000 and were thus essentially separated from the MP$_2$ proteins during gel filtration. The MP$_2$ fractions I-IV were concentrated using an ultrafilter (supplied by Amicon) with PM-10 membranes.

4. Final purification of the MP$_2$ fractions by inverse immunoadsorption

Some of the MP$_2$ fractions obtained from gel filtration were still contaminated by traces of MP$_1$ and immunoglobulins, while fraction III still contained ferritin in particular. These impurities could be removed by inverse immunoadsorption, i.e. using carrier-bound antibodies against these accompanying proteins. The purified protein solutions were then dialyzed against water and freeze-dried.

I claim:
1. Proteins MP$_2$ having the following characteristics:
 (a) an electrophoretic mobility in the range between that of $\alpha_2$ and that of $\beta_1$ globulins;
 (b) an isoelectric point in the pH range 4.4–5.0;
 (c) a sedimentation coefficient $s_{20W}{}^c$ in the range from 7 to above 20 S, the main fractions (IV, III, II and I) sedimenting at about 7, 9, 14 and 20 S respectively;
 (d) molecular weights in the range from 200,000 to 1,000,000, the main fractions (IV, III, II and I) having molecular weights of about 210,000, 400,000, 750,000 and 1,000,000;
 (e) an extinction coefficient $E_{1cm}{}^{1\%}$ (280 nm) of 12.5±0.2;
 (f) a carbohydrate content of 8.0±3.2% (mannose 1.4±0.4%, fucose 0.4±0.2%, galactose 1.2±0.4%, N-acetylglucosamine 2.6±1.8%, and N-acetylneuraminic acid 2.4±1.4%) and
 (g) an aminoacid composition in which aspartic acid, glutamic acid, leucine, valine, serine and glycine are among the aminoacids present in greatest amounts.

2. Process for obtaining the proteins MP$_2$ which have the following characteristics:
 (a) an electrophoretic mobility in the range between that of $\alpha_2$ and that of $\beta_1$ globulins;
 (b) an isoelectric point in the pH range 4.4–5.0;
 (c) a sedimentation coefficient $s_{20W}{}^c$ in the range from 7 to above 20 S, the main fractions (IV, III, II and I) sedimenting at about 7, 9, 14 and 20 S respectively;
 (d) molecular weights in the range from 200,000 to 1,000,000, the main fractions (IV, III, II and I) having molecular weights of about 210,000, 400,000, 750,000 and 1,000,000;
 (e) an extinction coefficient $E_{1cm}{}^{1\%}$ (280 nm) of 12.5±0.2;
 (f) a carbohydrate content of 8.0±3.2% (mannose 1.4±0.4%, fucose 0.4±0.2%, galactose 1.2±0.4%, N-acetylglucosamine 2.6±1.8%, and N-acetylneuraminic acid 2.4±1.4%) and (g) an aminoacid composition in which aspartic acid, glutamic acid, leucine, valine, serine and glycine are among the aminoacids present in greatest amounts.

which comprises extracting placental material, which has been extracted with physiological saline, using a solution containing 0.5 to 5 g of a non-ionic detergent per 100 ml, dialyzing the supernatent against water or buffer solution, further concentrating the solubilized placental tissue antigen, which is contained in the resulting solution, by immunoadsorption, subjecting the concentrated proteins in the resulting solution to gel filtration and essentially removing other proteins which have a smaller molecular weight and, where appropriate, removing accompanying proteins, which are still present as impurities, by inverse immunoadsorption and obtaining the $MP_2$ proteins.

3. The use of the proteins as claimed in claim 1 for the preparation of antibodies against these proteins for the detection and determination of these proteins and for diagnosis, monitoring the progress of a disease or checking therapy.

* * * * *